(12) United States Patent
Oduncu

(10) Patent No.: US 11,903,880 B2
(45) Date of Patent: Feb. 20, 2024

(54) GLAUCOMA TREATMENT EYEGLASS WITH VISUAL STIMULATION

(71) Applicants: Veysel Ozkapici, Istanbul (TR); Abdulkadir Oduncu, Istanbul (TR)

(72) Inventor: Abdulkadir Oduncu, Istanbul (TR)

(73) Assignee: GLAUCOT TEKNOLOJI ANONIM SIRKETI, Istanbul (TR)

( * ) Notice: Subject to any disclaimer, the term of this patent is extended or adjusted under 35 U.S.C. 154(b) by 1188 days.

(21) Appl. No.: 16/495,897

(22) PCT Filed: May 15, 2017

(86) PCT No.: PCT/TR2017/050193
§ 371 (c)(1),
(2) Date: Sep. 20, 2019

(87) PCT Pub. No.: WO2018/174835
PCT Pub. Date: Sep. 27, 2018

(65) Prior Publication Data
US 2020/0030150 A1    Jan. 30, 2020

(30) Foreign Application Priority Data
Mar. 20, 2017   (TR) ................................ 2017/04117

(51) Int. Cl.
*G02C 5/00* (2006.01)
*A61B 3/00* (2006.01)
(Continued)

(52) U.S. Cl.
CPC .................. *A61F 9/02* (2013.01); *A61B 3/16* (2013.01); *A61B 5/0022* (2013.01);
(Continued)

(58) Field of Classification Search
CPC ....... A61B 3/16; A61B 5/0022; A61B 5/6803; A61F 9/02; A61F 9/00781; A61F 9/022;
(Continued)

(56) References Cited

U.S. PATENT DOCUMENTS

| 2013/0238015 A1 | 9/2013 | Berdahl |
| 2014/0275935 A1 | 9/2014 | Walsh et al. |
| 2018/0279877 A1* | 10/2018 | Berdahl ............... A61B 5/6898 |

FOREIGN PATENT DOCUMENTS

| EP | 2098261 A2 * | 9/2009 | ............ A61M 21/00 |
| WO | WO-2015054681 A1 * | 4/2015 | ............ A61B 5/002 |

(Continued)

*Primary Examiner* — Mahidere S Sahle
(74) *Attorney, Agent, or Firm* — Bayramoglu Law Offices LLC

(57) ABSTRACT

A glaucoma treatment eyeglass with visual stimulation includes the parts of visually stimulating screen, pressure control unit, electronic control and communication unit, information display, pressure control valve, eyeglass cavity pressure sensor, flexible sealing gasket, pressure control buttons, electronic control buttons, pressure pipes, external pressure control unit, actively stimulating light source, mini notice screen, mobile device and notice lamp, which patients with glaucoma eye disease may use during the day, increasing the ocular flow of blood by means of visual stimulus according to the condition and level of the disease, decreasing the neurodegenerative effects and ensuring pressure control.

16 Claims, 9 Drawing Sheets

(51) Int. Cl.
*A61B 3/10* (2006.01)
*A61F 9/02* (2006.01)
*A61B 3/16* (2006.01)
*A61B 5/00* (2006.01)
*A61F 9/08* (2006.01)
*A61F 9/007* (2006.01)
*A61H 5/00* (2006.01)

(52) U.S. Cl.
CPC .......... *A61F 9/00781* (2013.01); *A61F 9/022* (2013.01); *A61F 9/08* (2013.01); *A61H 5/00* (2013.01); *A61B 5/6803* (2013.01); *A61F 9/029* (2013.01); *A61H 2201/5043* (2013.01); *A61H 2201/5071* (2013.01)

(58) Field of Classification Search
CPC .. A61F 9/08; A61F 9/029; A61H 5/00; A61H 2201/5043; A61H 2201/5071
USPC .................. 351/178, 203, 211; 600/398, 558
See application file for complete search history.

(56) References Cited

FOREIGN PATENT DOCUMENTS

WO    WO-2015068168 A1 *  5/2015  ............... A61H 5/00
WO        2017035406 A2    3/2017

* cited by examiner

GLAUCOMA TREATMENT EYEGLASS WITH VISUAL STIMULATION

CROSS REFERENCE TO THE RELATED APPLICATIONS

This application is the national phase entry of International Application No. PCT/TR2017/050193, filed on May 15, 2017, which is based upon and claims priority to Turkish Patent Application No. 2017/04117, filed on Mar. 20, 2017, the entire contents of which are incorporated herein by reference.

TECHNICAL FIELD

Invention is related to a glaucoma treatment eyeglass with visual stimulation, which patients with glaucoma eye disease may use during the day, decreasing the neurodegenerative effects and ensuring pressure control by increasing the ocular blood flow by means of a visual stimulus according to the situation and level of the disease.

BACKGROUND

Eye is a sense organ consisting of a sclerotic tissue (sclera) suitable to propagation and refraction of light, vein and retina. There are sensitive nerves of vision that may transmit the image to brain by means of the eyesight cells ensuring the event of vision in the eye. The stimuli received by the sensitive cells of vision in the eye are transmitted to the sensorium of vision of the brain by means of the sensitive nerves of vision and the incoming stimuli are evaluated there to result of the event of vision.

As with many organs, when eyes fail to perform their function fully or perform their function deficiently, diseases appear. The disorders such as amblyopia, cataract, color deficiency or glaucoma may be example of eye diseases. The disease of glaucoma is caused by the increase of the intraocular pressure in the eye because intraocular fluid fails to drain away well, known to public as eye pressure. The disorder of glaucoma causes vision loss in case it is not treated. In glaucoma, intraocular fluid pressure is high at such level at which it may damage the optic nerve which is necessary for the eyesight in general. This disease is the most frequently seen cause of visual loss in the world.

It is not possible to remove fully the disease of glaucoma. It is possible to prevent from it advancing by keeping it under control only. The methods of treatment administered in a person with eye pressure (glaucoma) are medical (eye drops), surgical and laser treatment. In the existing technique, there is an eyeglass developed for the treatment of the disorder of glaucoma. The US patent document with publication number US20130238015 A1 mentions about an eyeglass aiming at treating the disease of glaucoma with adjustment of pressure in the eyeglass cavity only. By means of this technique, a controlled volume is formed between eye and face through the eyeglass and by changing the pressure values of this cavity (the volume formed), one aims at controlling the pressure values on the bulbus oculi.

In order for visual stimulus to be formed, the glaucoma treatment eyeglass with visual stimulation developed using LCD screens and/or LED light sources ensures the increase of the speed of ocular blood flow in the eye in a controlled pressure environment and the neurodegenerative changes to be pressured in the visual cortex of brain being the visual brain cortex. Such an invention, namely the glaucoma treatment eyeglass ensures all the data and measurements to be transferred transiently to the suitable mobile devices, applications and similar media to be monitored by users or the physician. Thus, the opportunities of traceability, personalization of the treatment and intervening in the treatment transiently increase.

SUMMARY

The invention provides advantage for treating the glaucoma eye disease through daily use. By means of the glaucoma treatment eyeglass with visual stimulation, the hemianopsia is prevented by means of negative pressure and/or active and/or passive light stimuli to be applied to the eyes of patients. Thus, it is ensured that patient undergoing glaucoma treatment may see healthily. Furthermore, addition of visual stimulus increases the ocular flow of blood and decreases the neurodegenerative effect thereby benefit is provided for the visual nerves and visual brain cortex.

This invention is also capable of measuring the ambient pressure. By means of the micro controller available in it for orbital cavity, it calculates the most suitable pressure value and is capable of applying it to the eye of the patient.

The invention has the feature of communication with any mobile device. Such an invention, namely the glaucoma treatment eyeglass with visual stimulation, allows patients to share the results of measurement with his/her physician. The glaucoma treatment eyeglass with visual stimulation gives warning in case the eye of the patient reaches unwanted visual stimuli and pressure values outside the determined limits. All this information is kept recorded in the memory of the eyeglass and in the external module.

The structural and characteristic features of the invention and all its advantages will be understood more clearly thanks to the figure given and the detailed explanation written below and therefore the evaluation needs to be made taking into consideration this figure and detailed explanation.

Figure 1:
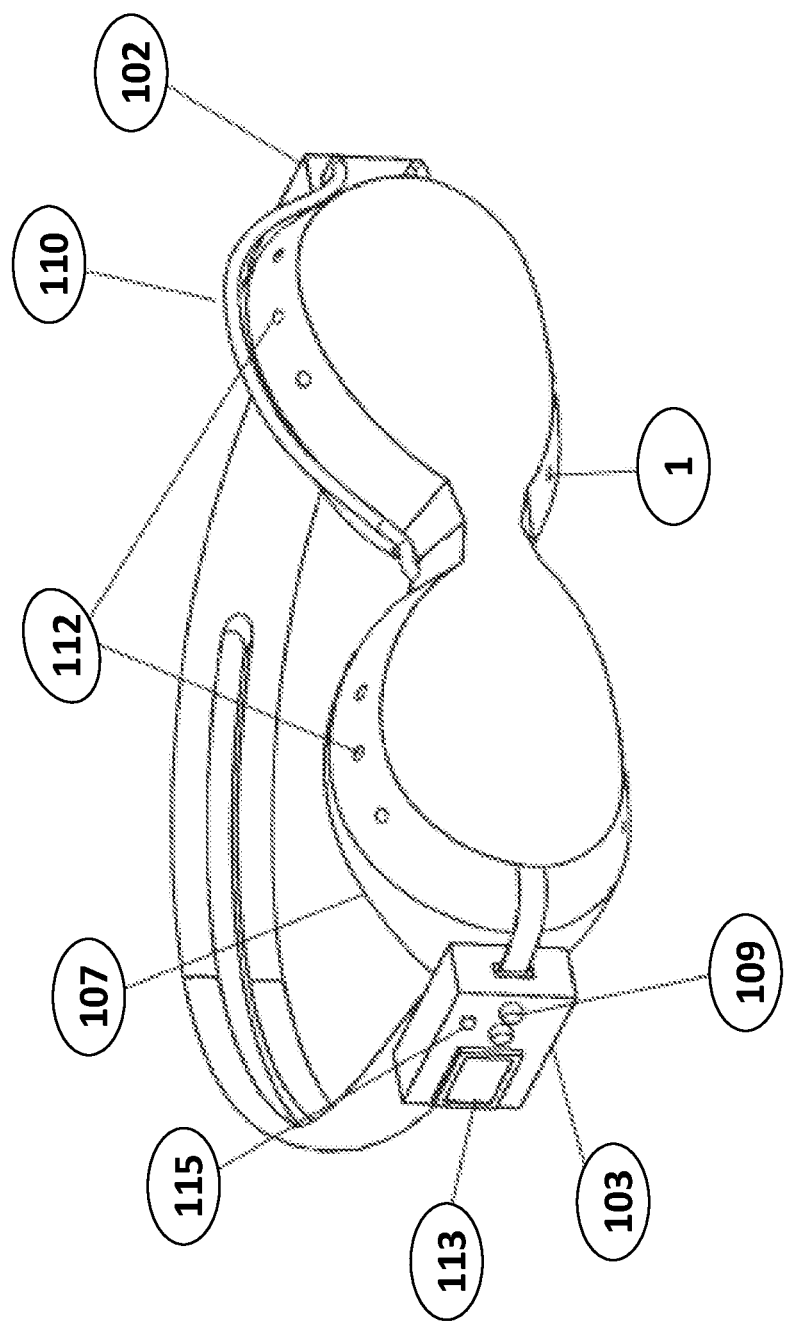
FIG. 1 shows the view of application of the glaucoma treatment eyeglass with visual stimulation together with the actively stimulating light source and pressure control unit.
Figure 2:
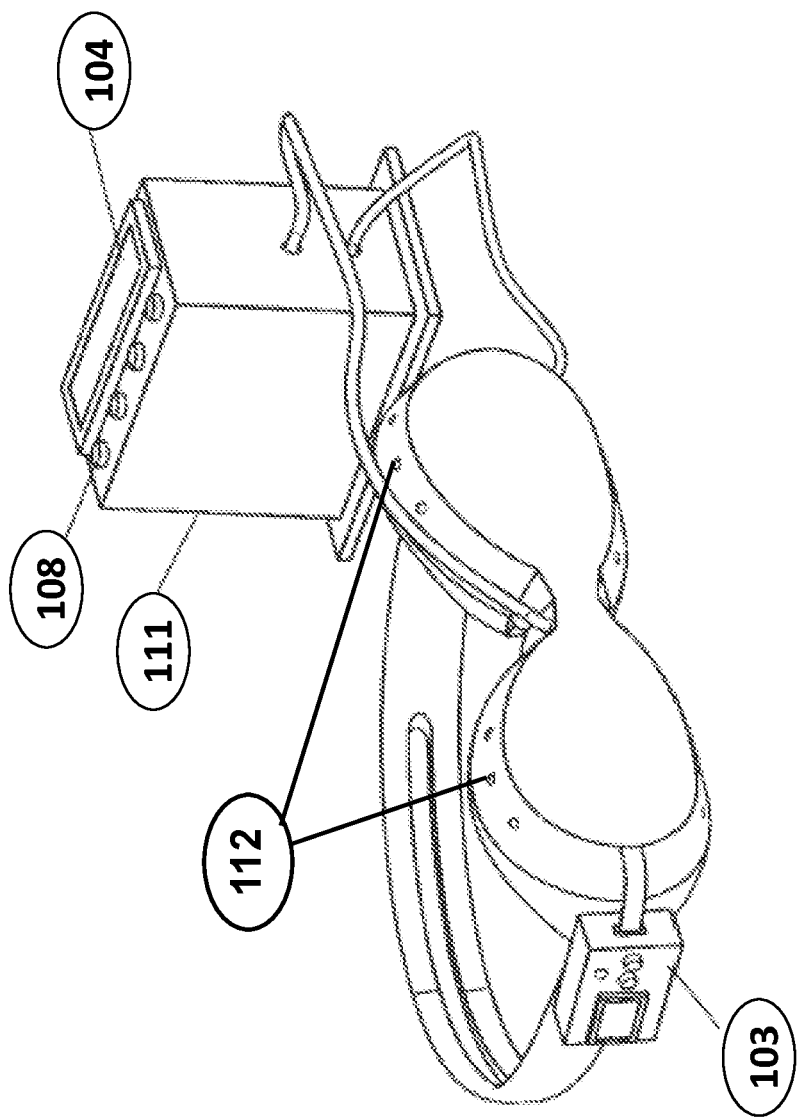
FIG. 2 shows the view of application of the glaucoma treatment eyeglass with visual stimulation together with the actively stimulating light source and external pressure control unit.
Figure 3:
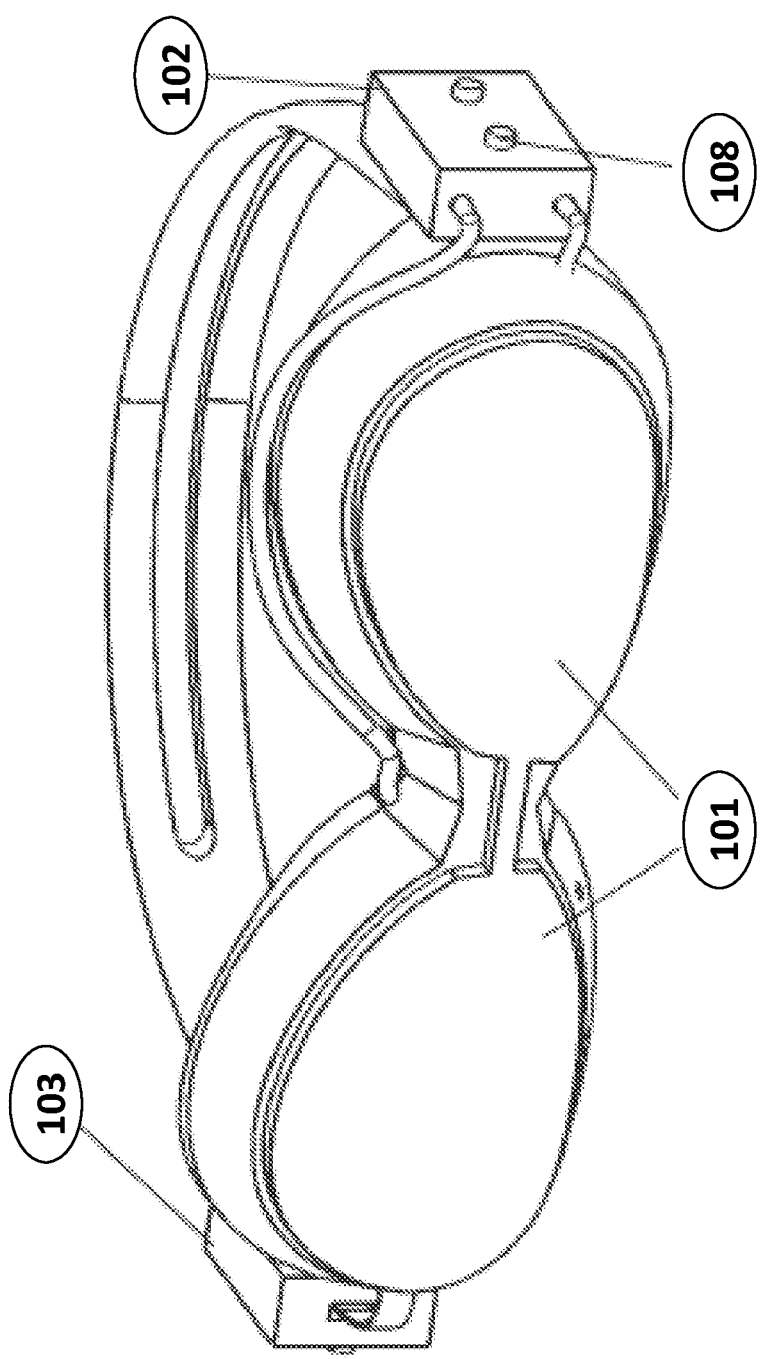
FIG. 3 shows the view of application of the glaucoma treatment eyeglass with visual stimulation together with visually stimulating screen and pressure control unit.
Figure 4:
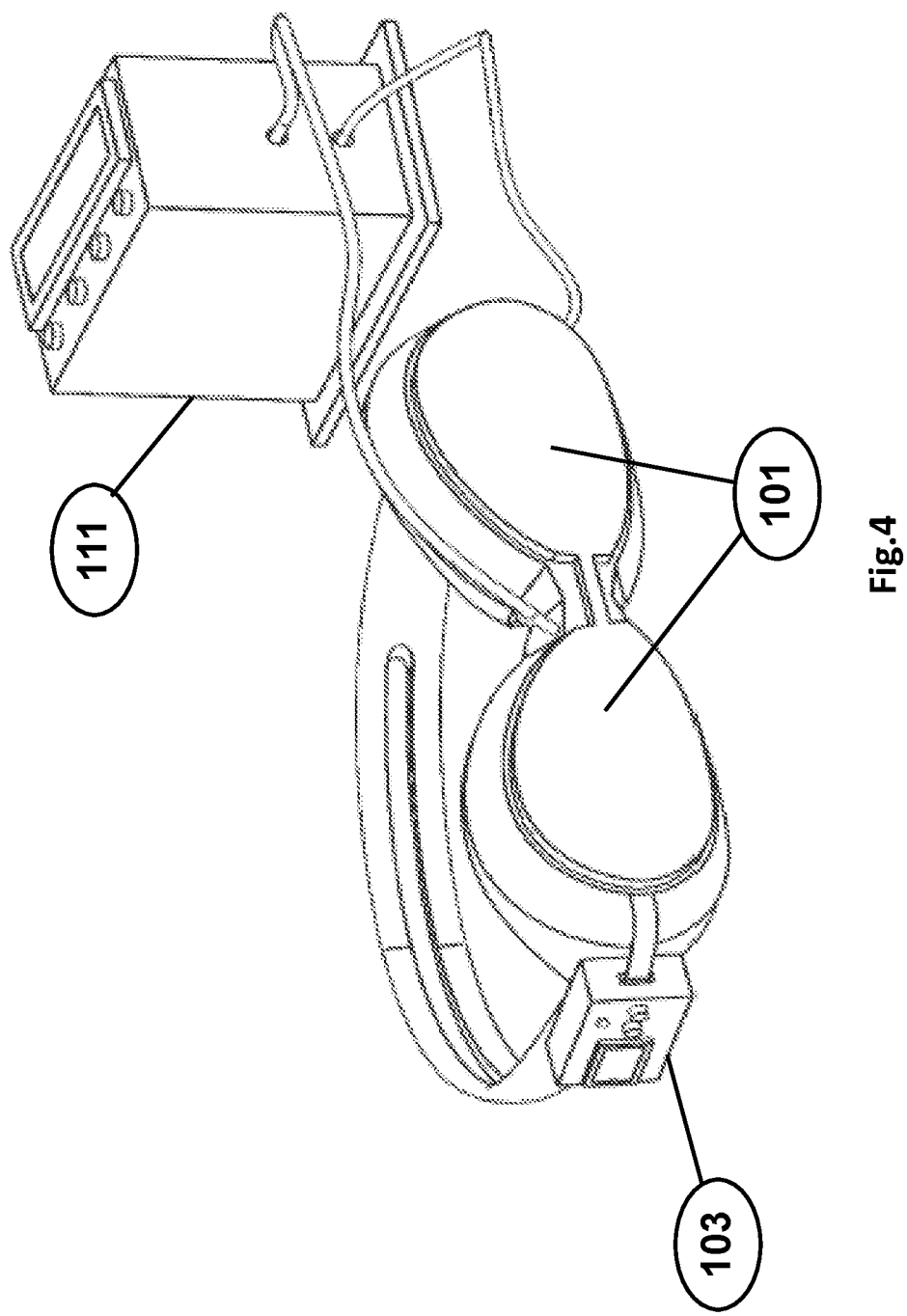
FIG. 4 shows the view of application of the glaucoma treatment eyeglass with visual stimulation together with visually stimulating screen and external pressure control unit.
Figure 5:
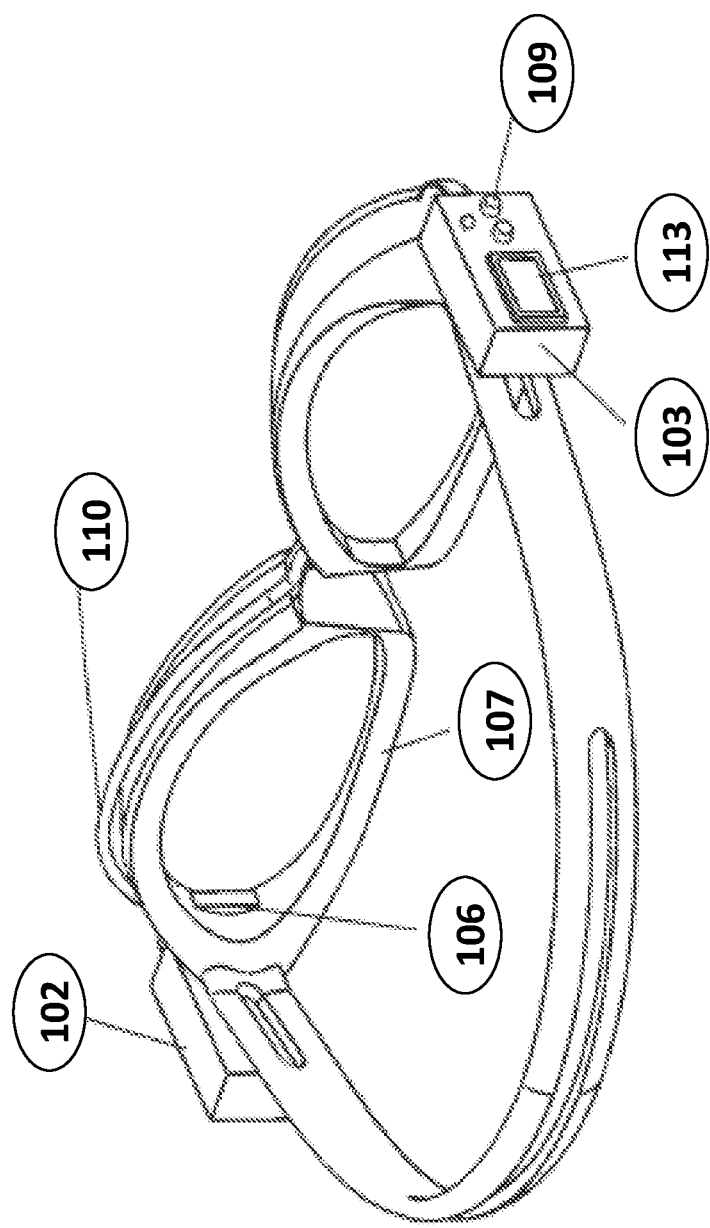
FIG. 5 shows the view of the demonstration of the eyeglass cavity pressure sensor inside the glaucoma treatment eyeglass with visual stimulation and flexible sealing gasket.
Figure 6:
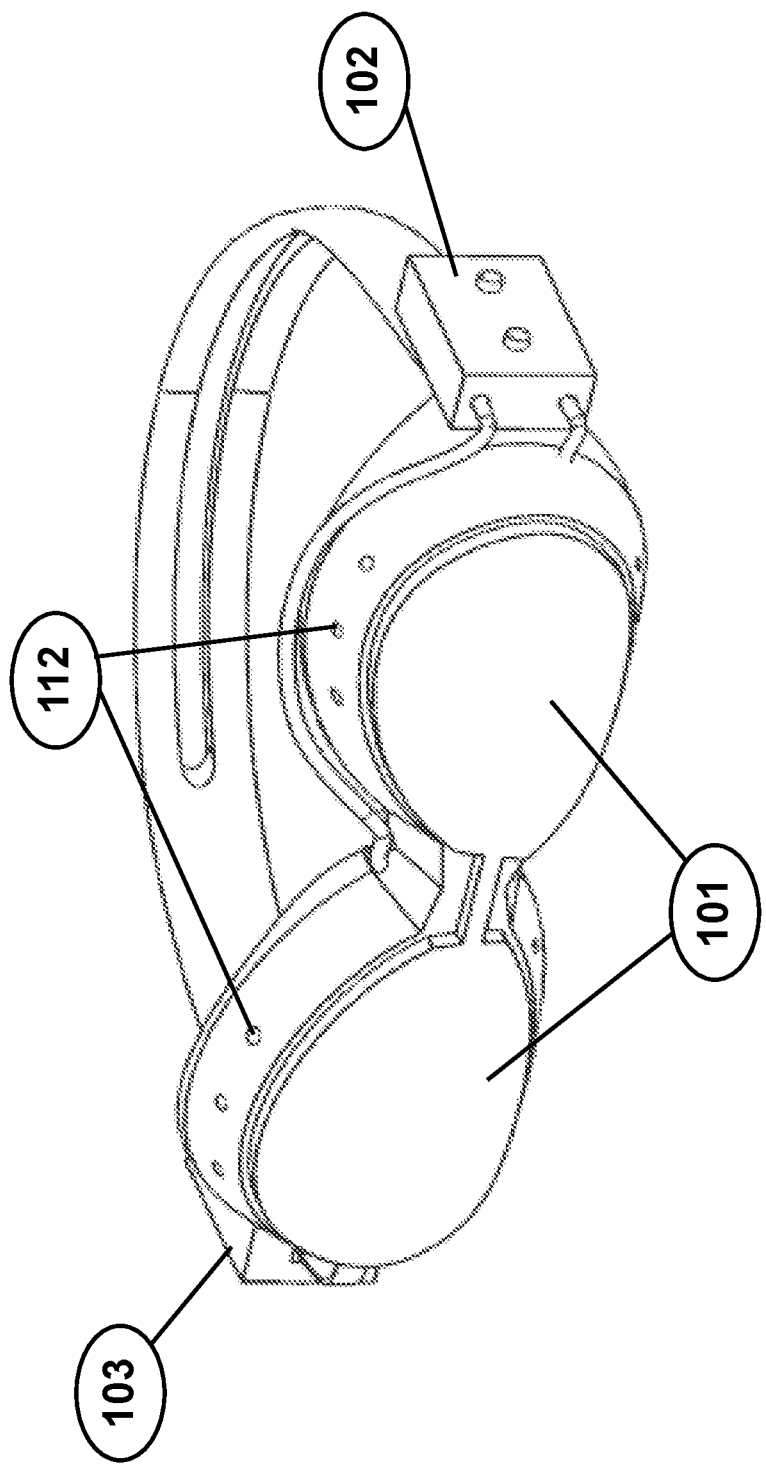
FIG. 6 shows the view of application of the glaucoma treatment eyeglass with visual stimulation together with both visual stimulating screen and actively stimulating light source and pressure control unit.
Figure 7:
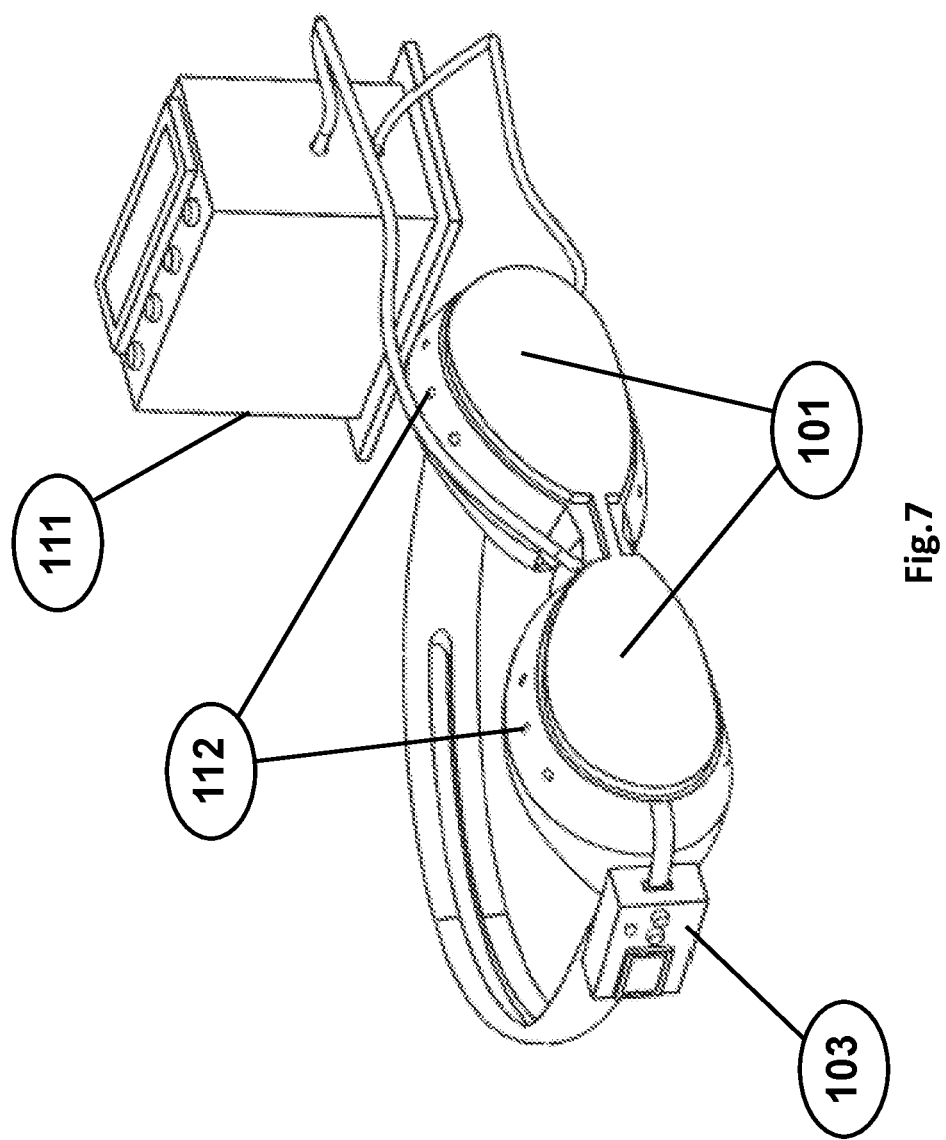
FIG. 7 shows the view of application of the glaucoma treatment eyeglass with visual stimulation together with both visually stimulating screen and actively stimulating light source and external pressure control unit.
Figure 8:
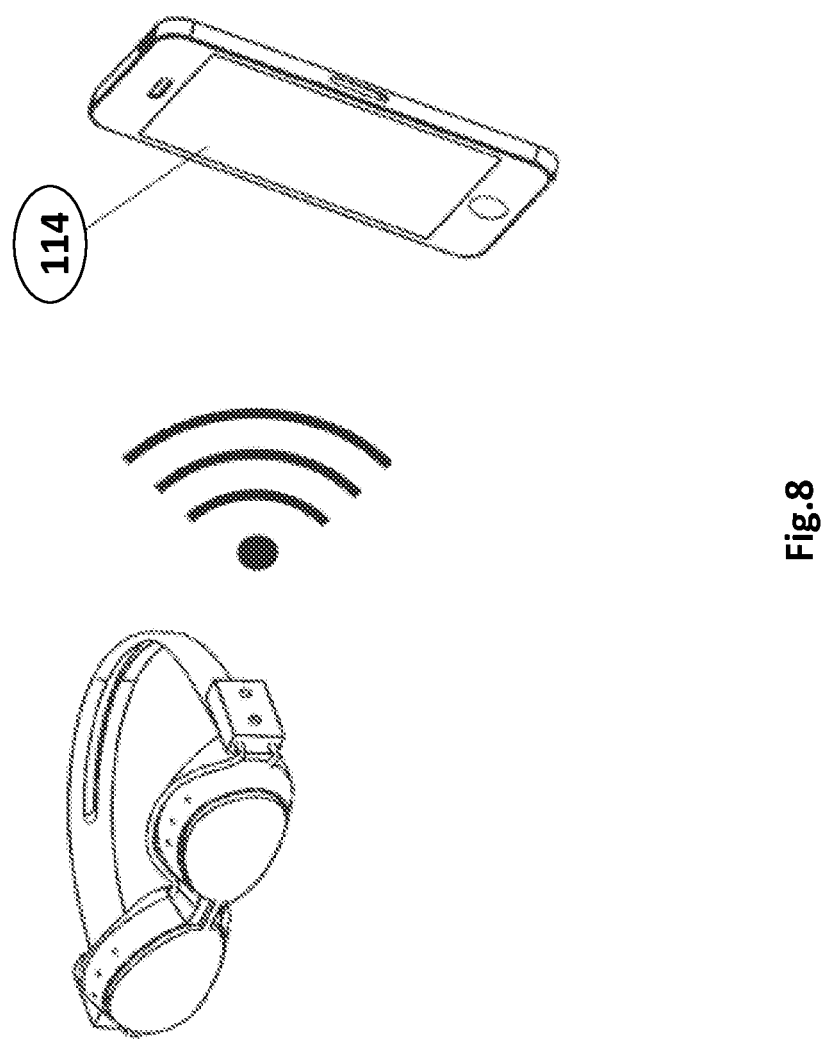
FIG. 8 shows the view of the glaucoma treatment eyeglass with visual stimulation in relation to it being capable of communicating electronically with any mobile device.

The reference numbers are illustrated as below:
101. Visually stimulating screen
102. Pressure control unit
103. Electronic control and communication unit
104. Information display
105. Pressure control valve
106. Eyeglass cavity pressure sensor
107. Flexible sealing gasket
108. Pressure control buttons
109. Electronic control buttons
110. Pressure pipes
111. External pressure control unit
112. Actively stimulating light source
113. Mini notice screen
114. Mobile device
115. Notice lamp

DETAILED DESCRIPTION OF THE EMBODIMENTS

The invention, namely the a glaucoma treatment eyeglass with visual stimulation, consists of the parts of visually stimulating screen (101), pressure control unit (102), electronic control and communication unit (103), information display (104), pressure control valve (105), eyeglass cavity pressure sensor (106), flexible sealing gasket (107), pressure control buttons (108), electronic control buttons (109), pressure pipes (110), external pressure control unit (111), actively stimulating light source (112), mini notice screen (113), mobile device (114) and notice lamp (115).

The invention increases the retinal flow of blood and decreases the neurodegenerative effect by means of the visually stimulating screen (101). The invention is also used in treatment of the glaucoma disease by changing and balancing the pressure on the bulbus oculi. The invention provides convenience for use by taking the shape to every face easily due to the flexible sealing gasket (107) on it.

The visual stimulus on the glaucoma treatment eyeglass with visual stimulation may be made as active or passive stimulus. Passive stimuli are in the form of the vision either being prevented or not prevented through the eyeglass screen using the visually stimulating screen (101). Active stimuli are in the form that, active stimulus light source (112) and light stimuli formed with systems emit active light through the eye. In visual stimulus, only passive sources, only active sources or a combination of the two together may be used. The purpose of active or passive stimulation created in the visual field is to speed up the ocular flow of blood and ensure the effect of healing the neurodegenerative effect. The visual stimulation feature of the invention ensures that the level of the disease is determined and the glaucoma treatment is administered specific to the person.

Figure 9:
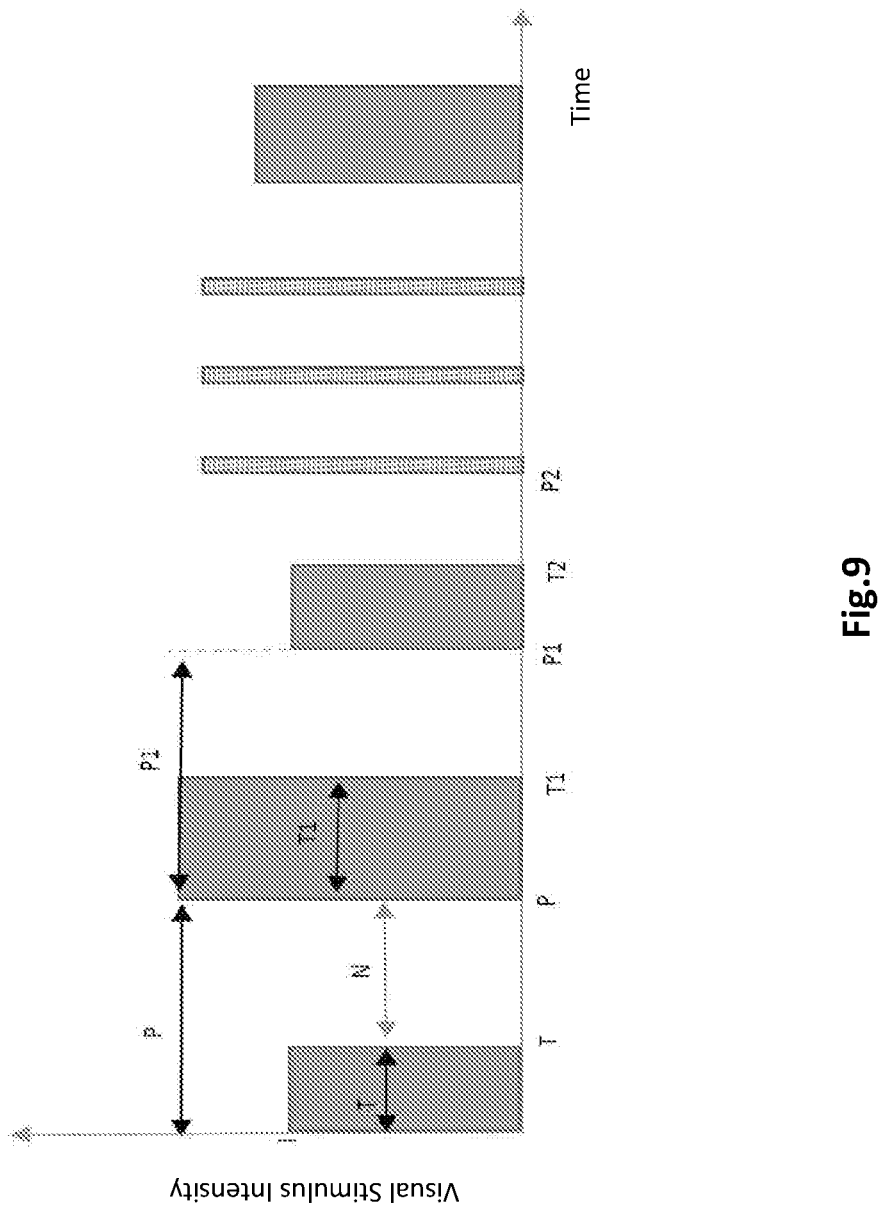
FIG. 9 shows a graph showing the change of the visual stimulus strength over time.

FIG. 9 shows a graph of the sample working method of the visual stimulus cycle according to stimulus strength changing over time, stimulus density and active/passive stimulus source. The visually stimulating screen (101) is dark or transparent within the working cycle. The visually stimulating screen (101) to be used for passive stimulation has been formed using LCD screen and is available on the front section of the glaucoma treatment eyeglass with visual stimulation. The working cycle of actively stimulating light source (112) is in the form of giving or not giving light. The actively stimulating light source (112) to be used for active stimulation has been formed using LED and similar light sources and is available on the side sections of the eyeglass or on the eyeglass.

On the graph shown in FIG. 9, the time when the visually stimulating screen (101) is dark is stated as T while the time when it is bright or transparent is stated as N. The total time when the visually stimulating screen (101) is dark and the time when it is light or transparent has been defined as the stimulation period P. This definition is also valid for active stimuli formed with the actively stimulating light source (112). In active stimulation, the time when the actively stimulating light source (112) gives light is named T while it does not give light is named N and the total of these two times is named P. This situation is stated mathematically as T+N=P. The period of the visual stimulus applied with the visually stimulating screen (101) and/or actively stimulating light source (112) may vary between 1 to 0.02 sec. or 1 to 50 Hz. The values of this period may be determined in the form repeating each other or in such a way that the value of each period will be different.

The rate of the stimulation time of the visually stimulating screen (101) and/or the actively stimulating light source (112) to the total time in the determined period is named duty cycle. This expression is stated mathematically so that it shall be D=T/P. During the treatment administered using the glaucoma treatment eyeglass with visual stimulation, the duty cycle named D may be applied independently, as determined variable or so that they will be same with each other. The value D (duty cycle) may vary between 0.01 and 0.99.

The stimulus intensity in the period in graph shown in FIG. 9 is defined as I. The stimulus intensity (I) is between 10% to 100% on the visually stimulating screen (101) developed using LCD and between the range of 0.01 mW to 10 W when darkness level and/or the actively stimulating light source (112) is used. On the glaucoma treatment eyeglass with visual stimulation, the light sources in the wavelength of 400-700 nm are used as the actively stimulating light source (112). LED light sources are the best example to this situation.

As seen from the graph shown in FIG. 9, fully filled blocks represent the visually stimulating screen (101) developed using LCD. During the blocks stated in thick format, the visually stimulating screen (101) is dark. In other periods, the screen is either light or transparent. In this case, the glaucoma treatment eyeglass with visual stimulation provides passive stimulation. Passive stimuli change in the same way with each other or change or repeat in the structure of a cycle specific to patient. The duty cycle and intensity of the stimulation in every period may be determined independently. The interruptedly filled blocks on graph shown in FIG. 9 represent the actively stimulating light source (112) developed using LED sources providing active stimulation. As seen from Graph 1, the time, period, intensity and form of the actively stimulating light source (112) change or repeat within a certain cycle.

The invention, namely the glaucoma treatment eyeglass with visual stimulation, the visually stimulating screen (101) and the actively stimulating light source (112) may be used either on their own or together. By means of the visually stimulating screen (101), the visual field is stimulated passively while, by means of the actively stimulating light source (112), the visual field is stimulated actively. The value of the duty cycle D, its period and intensity in both visual stimuli may be determined according to person or certain conditions. These two visually stimulation forms can be used within a cycle determined together or separately.

The invention, namely the glaucoma treatment eyeglass with visual stimulation, the pressure control and change of the volume formed on the bulbus oculi may also be performed. The pressure control unit (102) on the eyeglass which is the subject of the invention provides the pressure control formed on the eyeglass cavities.

The invention, namely the glaucoma treatment eyeglass with visual stimulation, one of the two pressure control units is being used only. The pressure control unit (102) or the external pressure control unit (111) provides the pressure control separately for both eyes or the pressure control of a single cavity in which both eyes are included continuously thanks to the eyeglass cavity pressure sensor (106).

The eyeglass cavity pressure sensors (106) may measure both the intracranial pressure and intraocular pressure. Measuring also the ambient pressure, the eyeglass cavity pressure sensors (106) may perform comparison with the pressure of eyeglass cavities. The pressure value formed in the cavity with the help of the pressure control unit (102) or the external pressure control unit (111) is compared with the intraocular pressure and intracranial pressure values transiently and optimum conditions are ensured to be adjusted specific to person necessary for treatment of glaucoma. The pressure of the eyeglass cavities may be controlled by applying pressure specific to desire in the positive/negative direction by means of pressure pipes (110). In order for reference measurements to be able to be made and the pressure to be able to be equalized with external ambient in necessary conditions, pressure control valve (105) may be used.

The pressure control unit (102) or the external pressure control unit (111) keeps the pressure within the eyeglass cavity in the value determined specific to person in the range of +40 mmHg to −40 mmHg by calculating the most suitable pressure value with the processor in it. By means of the pressure control buttons (108) available on the pressure control unit (102) or the external pressure control unit (111), mode adjustments may be made. These modes are determined beforehand by physicians as per the situation of the eye of the patient or the pressure values of eyeglass cavities may be adjusted on time basis so that the same will be determined specific to person.

By means of the pressure control buttons (108) available on the pressure control unit (102) or the external pressure control unit (111), on/off, mode control and other necessary adjustments may be performed. The sharing of the information available on the pressure control unit (102) or the external pressure control unit (111) with user is realized as the data transfer of the information to a mobile device (114) thanks to a transmitting module within the electronic control and communication unit (103). Thus, the operation of the eyeglass, the subject of the invention and treatment process, may be followed up easily by both the patient and physician. By means of the electronic control buttons (109) available on the electronic control and communication unit (103), mode adjustments may be performed. Besides, the user may also perform the on/off procedure of the display. In case of any malfunction, the notice lamp (115) warns the user by flashing.

The glaucoma treatment eyeglass with visual stimulation both regulates the translaminar pressure difference by ensuring the balance between intraocular pressure and intracranial pressure for treatment of glaucoma patients and makes the treatment more effective by decreasing the neurodegenerative effects of the glaucoma disease and increasing the speed of ocular flow of blood. The types of visual stimulus stated in the invention may be used together with pressure control or individually.

Because of the subject invention, permanent visual losses of patients may be precluded. Patients with glaucoma eye disease may use the visual stimulus glaucoma treatment eyeglass comfortably during the day. The invention, namely glaucoma treatment eyeglass with visual stimulation, eliminates all the disadvantages in the existing technique and furthers the existing treatment techniques.

The techniques mentioned in each claim and all other specifications are followed by a reference number, which has been used for facilitating the understanding the claims only, hence, one should not consider that these limit the extent of any of the elements specified with these reference numbers for exemplification purposes.

It is obvious that a person who is expert in the technique may set forth the novelty put forward in the subject invention also using the similar structuring and/or apply this structuring to other areas with similar purpose used in the relevant technique. Therefore, it is also obvious that such structuring will be devoid of the criterion that the novelty and especially the known situation of the technique are surpassed.

What is claimed is:

1. A glaucoma treatment eyeglass with visual stimulation configured to be used by a plurality of patients in a plurality of periods during a day or for continual use, wherein the glaucoma treatment eyeglass with visual stimulation comprises:
    a visually stimulating screen,
    a pressure control unit,
    an electronic control and communication unit,
    an information display,
    an eyeglass cavity pressure sensor,
    a flexible sealing gasket,
    a plurality of pressure control buttons,
    a plurality of electronic control buttons,
    a plurality of pressure pipes,
    an actively stimulating light source,
    a mini notice screen, and
    a notice lamp;
    wherein the visually stimulating screen is connected with the pressure control unit via the plurality of pressure pipes; the visually stimulating screen is connected with the electronic control and communication unit the pressure control buttons and the information display are located on the pressure control unit the mini notice screen, the plurality of electronic control buttons, and the notice lamp are provided on the electronic control and communication unit the eyeglass cavity pressure senor is provided inside the glaucoma treatment eyeglass, the flexible sealing gasket is provided on the glaucoma treatment eyeglass and is configured to take the shape of a face of a user, and the actively stimulating light source is provided on the glaucoma treatment eyeglass;
    wherein the glaucoma treatment eyeglass with visual stimulation is configured to increase an ocular flow of blood through a visual stimulus according to a condition and a level of a disease, and decrease a neurodegenerative effects and ensues a pressure control, and
    wherein the plurality of pressure pipes control the pressure of the eyeglass cavities by applying a desired negative or positive pressure generated by the pressure control unit.

2. The glaucoma treatment eyeglass with visual stimulation according to claim 1, wherein the visually stimulating screen is provided on a front section of the glaucoma treatment eyeglass with visual stimulation; wherein the visual stimulating screen is an LCD display; wherein during a cycle a plurality of passive stimuli repeat each other in a same way in a visual field or forming a different passive stimulus to continue as an independent closure period or a brightness period, a visual stimulus frequency varies between 1 to 50 Hz, a stimulus intensity is adjusted as a darkness level between 10% to 100% in the passive stimulus, with a duty cycle value being a rate of stimulation time to a total time in a determined period changing between 0.01 to 0.99.

3. The glaucoma treatment eyeglass with visual stimulation according to claim 1, wherein the actively stimulating light source includes a plurality of LED sources having a wavelength of 400-700 nm, thereby ensuring the visual field to be stimulated actively, and wherein a value of a duty cycle and a sequencing of the stimuli is determined according to a person or a condition of the disease, and a stimulus intensity varies between 0.01 mW to 10 W and a frequency thereof varies in a range of 1 HZ to 50 Hz.

4. The glaucoma treatment eyeglass with visual stimulation according to claim 1, wherein the pressure control unit provides the pressure control separately for both eyes or the pressure control of a single cavity; wherein the eyeglass cavity pressure sensor is configured to make the pressure control of eyeglass cavities continuously, make comparison with a pressure of eyeglass cavities by measuring an ambient pressure and is configured to keep a pressure in the eyeglass cavity in a value between +40 mmHg to −40 mmHg by calculating a most suitable pressure value with a processor and save a usage information of a patient and a plurality of pressure values measured transiently and give an information to the patient.

5. The glaucoma treatment eyeglass with visual stimulation according to claim 1, wherein the eyeglass cavity pressure sensor is configured to adjust a plurality of optimum conditions specific to the person necessary for a treatment of glaucoma by comparing the pressure value formed in an eyeglass cavity with the pressure control unit or the external pressure control unit by measuring an intracranial pressure and an intraocular pressure values transiently.

6. The glaucoma treatment eyeglass with visual stimulation according to claim 1, wherein the plurality of pressure control buttons ensure a plurality of pressure values of eyeglass cavities are made on time basis according to the condition of the eye of the patient, and enabling a plurality of mode adjustments to be made in terms of the pressure control unit.

7. The glaucoma treatment eyeglass with visual stimulation according to claim 1, wherein the electronic control and communication unit share information available on the pressure control unit with a user and transfer the information to a mobile device by a transmitting module.

8. The glaucoma treatment eyeglass with visual stimulation according to claim 1, wherein the plurality of electronic control buttons ensure a plurality of mode adjustments of the electronic control and the communication unit.

9. The glaucoma treatment eyeglass with visual stimulation according to claim 1, wherein the notice lamp is configured to flash in case of any malfunction to warn the user.

10. The glaucoma treatment eyeglass with visual stimulation according to claim 4, wherein the eyeglass cavity pressure sensor is configured to adjust a plurality of optimum conditions specific to the person necessary for a treatment of glaucoma by comparing the pressure value formed in an eyeglass cavity with the pressure control unit by measuring an intracranial pressure and an intraocular pressure values transiently.

11. The glaucoma treatment eyeglass with visual stimulation according to claim 4, wherein the plurality of pressure control buttons ensure a plurality of pressure values of eyeglass cavities to be made on time basis according to the condition of the eye of the patient, and enabling a plurality of mode adjustments to be made in terms of the pressure control unit.

12. The glaucoma treatment eyeglass with visual stimulation according to claim 4, wherein the electronic control and the communication unit share information available on the pressure control unit or the external pressure control unit with a user and transfer the information to a mobile device by a transmitting module.

13. The glaucoma treatment eyeglass with visual stimulation according to claim 7, wherein the plurality of electronic control buttons are provided on the electronic control and the communication unit, to ensure a the plurality of mode adjustments of the electroniccontrol and the communication unit.

14. The glaucoma treatment eyeglass with visual stimulation according to claim 1, wherein the pressure control unit is an external pressure control unit.

15. The glaucoma treatment eyeglass with visual stimulation according to claim 2, wherein the visual stimulus frequency is about 40 Hz.

16. The glaucoma treatment eyeglass with visual stimulation according to claim 3, wherein the frequency is about 40 Hz.

* * * * *